United States Patent
Yokota

(10) Patent No.: US 10,368,721 B2
(45) Date of Patent: *Aug. 6, 2019

(54) ENDOSCOPE

(71) Applicant: OLYMPUS CORPORATION, Hachioji-shi, Tokyo (JP)

(72) Inventor: Masayoshi Yokota, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 152 days.

This patent is subject to a terminal disclaimer.

(21) Appl. No.: 15/450,741

(22) Filed: Mar. 6, 2017

(65) Prior Publication Data

US 2017/0172384 A1 Jun. 22, 2017

Related U.S. Application Data

(63) Continuation of application No. 14/078,223, filed on Nov. 12, 2013, now Pat. No. 9,622,644, which is a
(Continued)

(30) Foreign Application Priority Data

May 24, 2011 (JP) .................................. 2011-116140

(51) Int. Cl.
*A61B 1/05* (2006.01)
*A61B 1/00* (2006.01)
*A61B 1/06* (2006.01)

(52) U.S. Cl.
CPC ...... *A61B 1/00009* (2013.01); *A61B 1/00045* (2013.01); *A61B 1/00096* (2013.01);
(Continued)

(58) Field of Classification Search
CPC ... A61B 1/00009; A61B 1/00045; A61B 1/06; A61B 1/0661; A61B 1/00096; A61B 1/05
See application file for complete search history.

(56) References Cited

U.S. PATENT DOCUMENTS

| | | | |
|---|---|---|---|
| 5,150,254 A | | 9/1992 | Saitou |
| 5,434,669 A | * | 7/1995 | Tabata .................. A61B 1/042 356/241.5 |

(Continued)

FOREIGN PATENT DOCUMENTS

| | | |
|---|---|---|
| DE | 10104483 A1 | 10/2002 |
| EP | 2106748 A1 | 10/2009 |

(Continued)

OTHER PUBLICATIONS

European Office Action dated Apr. 4, 2016, issued in counterpart European Application No. 12777405.7.
(Continued)

*Primary Examiner* — Tung T Vo
*Assistant Examiner* — Joseph W Becker
(74) *Attorney, Agent, or Firm* — Holtz, Holtz & Volek PC

(57) ABSTRACT

An endoscope configured to measure a specimen using a stripe image formed by projecting a light-dark pattern on the specimen, the endoscope including an insertion portion having an elongated shape; an imaging unit provided at a distal portion of the insertion portion and configured to acquire an image of the specimen; a lighting unit configured to illuminate an observation field of view of the imaging unit; and a pattern projector which emits projection light configured to project the light-dark pattern to the specimen and project the light-dark pattern on the specimen. The imaging unit includes an image sensor configured to image the image of the specimen; and an objective optical system configured to form the image of the specimen on the image sensor. The pattern projector includes a pattern generator configured to generate the light-dark pattern; and a projection optical system provided at the distal portion of the insertion portion and configured to emit the projection light to the specimen via the light-dark pattern. A radiation angle
(Continued)

of the projection light in the projection optical system is smaller than an angle of view of the objective optical system. The objective optical system is in focus at farther point side than a minimum object distance which is a minimum value of an object distance at which the entire projected light-dark pattern enters an imaging field of view of the image sensor.

11 Claims, 4 Drawing Sheets

Related U.S. Application Data continuation of application No. PCT/JP2012/063258, filed on May 24, 2012.

(52) U.S. Cl.
CPC ............... *A61B 1/05* (2013.01); *A61B 1/06* (2013.01); *A61B 1/0661* (2013.01)

(56) References Cited

U.S. PATENT DOCUMENTS

| | | | |
|---|---|---|---|
| 5,436,655 A | 7/1995 | Hiyama et al. | |
| 5,784,098 A | 7/1998 | Shoji et al. | |
| 6,419,626 B1 * | 7/2002 | Yoon ................ | A61B 1/00052 600/103 |
| 6,464,633 B1 | 10/2002 | Hosoda et al. | |
| 2005/0061062 A1 | 3/2005 | Kaneko et al. | |
| 2009/0225321 A1 | 9/2009 | Bendall et al. | |
| 2009/0225333 A1 | 9/2009 | Bendall et al. | |
| 2009/0244260 A1 | 10/2009 | Takahashi et al. | |
| 2010/0063355 A1 | 3/2010 | Matsuura | |
| 2010/0149315 A1 | 6/2010 | Qu et al. | |
| 2011/0267444 A1 | 11/2011 | Yamaguchi | |
| 2014/0052005 A1 | 2/2014 | Yokota | |
| 2014/0071239 A1 | 3/2014 | Yokota | |
| 2014/0071257 A1 | 3/2014 | Yokota | |

FOREIGN PATENT DOCUMENTS

| | | |
|---|---|---|
| EP | 2272417 A1 | 1/2011 |
| JP | 63200115 A | 8/1988 |
| JP | 01209415 A | 8/1989 |
| JP | 02085706 A | 3/1990 |
| JP | 02287311 A | 11/1990 |
| JP | 03128043 A | 5/1991 |
| JP | 05045132 A | 2/1993 |
| JP | 05211988 A | 8/1993 |
| JP | 09061132 A | 3/1997 |
| JP | 10239031 A | 9/1998 |
| JP | 10239034 A | 9/1998 |
| JP | 2005091265 A | 4/2005 |
| JP | 2007139822 A | 6/2007 |
| JP | 2007144024 A | 6/2007 |
| JP | 2008229025 A | 10/2008 |
| JP | 2009019941 A | 1/2009 |
| JP | 2009061014 A | 3/2009 |
| JP | 2009240621 A | 10/2009 |
| JP | 2009258273 A | 11/2009 |
| WO | 03105289 A2 | 12/2003 |
| WO | 2007102195 A1 | 9/2007 |

OTHER PUBLICATIONS

Extended European Search Report dated Apr. 15, 2014 in counterpart European Application No. 12789379.0.
Extended European Search Report dated May 20, 2014 in counterpart European Application No. 12777405.7.
Final Office Action dated Sep. 6, 2016, in U.S. Appl. No. 14/061,530.
International Search Report (ISR) dated Jul. 10, 2012, issued in counterpart International Application No. PCT/JP2012/063258.
International Search Report (ISR) dated Jul. 10, 2012, issued in counterpart International Application No. PCT/JP2012/063266.
International Search Report (ISR) dated Jul. 24, 2012, issued in counterpart International Application No. PCT/JP2012/060832.
Japanese Office Action (and English translation thereof) dated Mar. 3, 2015, issued in counterpart Japanese Application No. 2011-116141.
Japanese Office Action (and English translation thereof) dated May 7, 2015, issued in counterpart Japanese Application No. 2011-099889.
Office Action dated May 5, 2016, issued in U.S. Appl. No. 14/085,726.
U.S. Appl. No. 14/061,530; First Named Inventor: Masayoshi Yokota; Title: "Endoscope Apparatus and Measuring Method"; filed Oct. 23, 2013.
U.S. Appl. No. 14/078,223; First Named Inventor: Masayoshi Yokota; Title: "Endoscope"; filed Nov. 12, 2013.
U.S. Appl. No. 14/085,726; First Named Inventor: Masayoshi Yokota; Title: "Endoscope Device, and Measurement Method"; filed Nov. 20, 2013.
Non-Final Office Action dated Oct. 11, 2018 issued in U.S. Appl. No. 15/423,043.

* cited by examiner

ENDOSCOPE

This application is a Continuation Application of U.S. Ser. No. 14/078,223, filed Nov. 12, 2013, which is a Continuation Application based on PCT Patent Application No. PCT/JP2012/063258, filed May 24, 2012, whose priority is claimed from Japanese Patent Application No. 2011-116140, filed May 24, 2011, the contents of all of which are incorporated herein by reference.

BACKGROUND OF THE INVENTION

Field of the Invention

The present invention relates to an endoscope, and more particularly, to an endoscope configured to project a pattern such as stripes or the like on a specimen and measure a three-dimensional shape of a specimen surface.

Description of Related Art

In the related art, in order to inspect a specimen, an endoscope including an imaging unit which has an optical system, an image sensor, and the like, and is arranged at a distal end of a long insertion portion of the endoscope is used. In such endoscopes, a constitution in which a plurality of stripe images formed by projecting a stripe pattern on a specimen are acquired while offsetting a phase of the stripe pattern, and a three-dimensional shape of the specimen is calculated using the plurality of stripe images is known. For example, US Patent Publication Application, Publication No. 2009/0225321 discloses an endoscope having two projection windows which are configured to project stripes and are arranged at a distal surface of an insertion portion of the endoscope. The endoscope disclosed in US Patent Publication Application, Publication No. 2009/0225321 is configured such that the stripe pattern is displayed on the entire stripe image acquired by the imaging unit.

SUMMARY OF THE INVENTION

According to a first aspect of the present invention, an endoscope configured to measure a specimen using a stripe image formed by projecting a light and dark pattern on the specimen includes: an insertion portion having an elongated shape; an imaging unit provided at a distal portion of the insertion portion and configured to acquire an image of the specimen; a lighting unit configured to illuminate an observation field of view of the imaging unit; and a pattern projector having a light source configured to emit projection light to project the light and dark pattern on the specimen. The pattern projector generates a region, in which the light and dark pattern is not projected, in at least one end of a direction in which stripes of the light and dark pattern are arranged in an imaging field of view of the imaging unit, in a state in which the light and dark pattern is projected on the specimen.

According to a second aspect of the present invention, in the endoscope according to the first aspect, the imaging unit may include: an image sensor configured to image the image of the specimen; and an objective optical system configured to form the image of the specimen on the image sensor. The pattern projector may include: a pattern generator configured to generate the light and dark pattern; and a projection optical system provided at the distal portion of the insertion portion and configured to radiate the projection light from the light source to the specimen via the light and dark pattern. A radiation angle of the projection light in the projection optical system may be smaller than an angle of view of the objective optical system.

According to a third aspect of the present invention, in the endoscope according to the first or second aspect, in the state in which the region, in which the light and dark pattern is not projected, is generated in at least one end of the direction in which the stripes of the light and dark pattern are arranged in the imaging field of view of the imaging unit, the objective optical system may be in focus.

According to a fourth aspect of the present invention, in the endoscope according to any one of the first to third aspects, only one projection window configured to project the light and dark pattern on the specimen may be provided at a distal surface of the insertion portion.

According to a fifth aspect of the present invention, the endoscope according to any one of the first to fourth aspects may further include a display having a display screen configured to display the image of the specimen. The display may display a frame on the display screen, the frame showing a predicted projection position on the display screen of the stripe pattern projected on the specimen.

According to a sixth aspect of the present invention, the endoscope according to the fifth aspect may further include a controller configured to perform measurement of a three-dimensional shape of the specimen with respect to only a region disposed in the frame on the image displayed on the display screen.

DETAILED DESCRIPTION OF THE INVENTION

Hereinafter, an endoscope and a measurement method according to an embodiment of the present invention are described.

Figure 1:
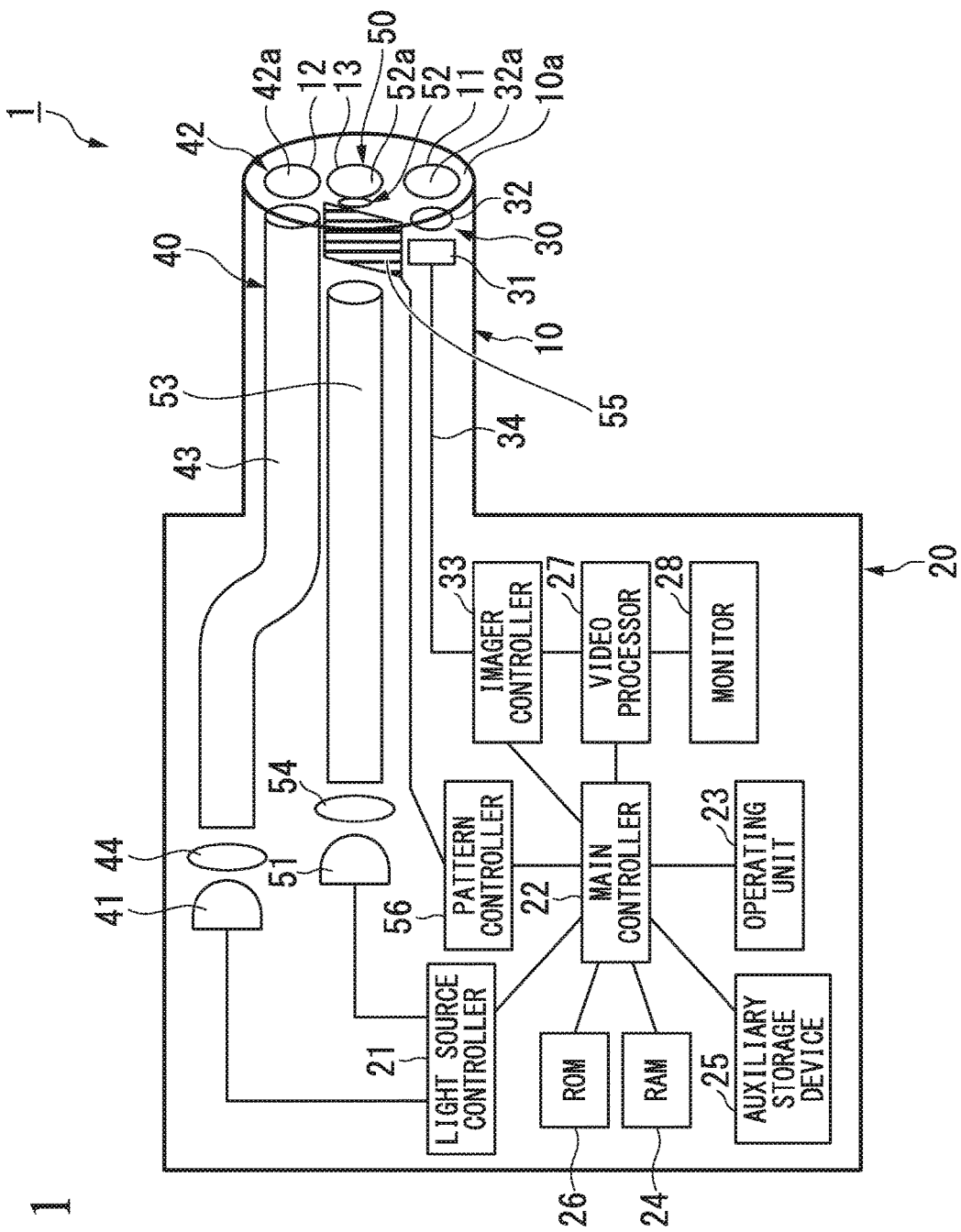
FIG. 1 is a block diagram showing a constitution of an endoscope according to an embodiment of the present invention.
Figure 2:
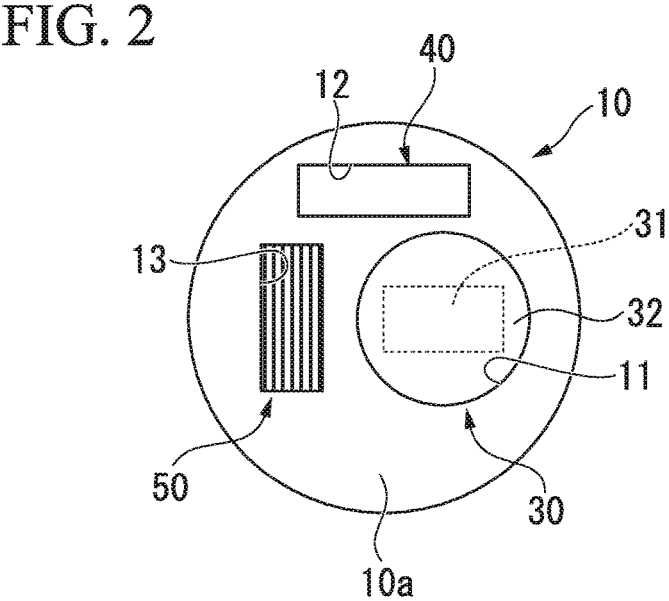
FIG. 2 is a front view showing a distal surface of an insertion portion of the endoscope according to the embodiment of the present invention.

First, a constitution of an endoscope 1 according to the embodiment is described. FIG. 1 is a block diagram showing the constitution of the endoscope 1. FIG. 2 is a front view showing a distal surface of an insertion portion 10 of the endoscope 1.

The endoscope 1 is a measurement endoscope configured to measure a specimen using a pattern projection image formed by projecting a light and dark pattern on the specimen. In addition, the endoscope 1 is used for internal observation of the specimen, observation of the specimen disposed at a position that a conventional observation device cannot easily access, or the like.

As shown in FIG. 1, the endoscope 1 includes the insertion portion 10 having an elongated shape, and a main body portion 20 to which a distal end of the insertion portion 10 is connected.

The insertion portion 10 is formed in a tubular shape. The insertion portion 10 is inserted into the inside of the specimen or an access path to the specimen. The insertion portion 10 is provided with an imaging unit 30, a lighting unit 40, and a pattern projector 50. The imaging unit 30 acquires the image of the specimen. The lighting unit 40 illuminates an observation field of view in front of the insertion portion 10. The pattern projector 50 projects the light and dark pattern on the specimen. In the embodiment, the pattern projector 50 projects the stripe pattern, as a light and dark pattern, on the specimen.

As shown in FIG. 2, an opening 11, a lighting window 12, and a projection window 13 are provided at a distal surface 10a of the insertion unit 10. The opening 11 allows external light to enter an objective optical system 32 of the imaging unit 30. The lighting window 12 radiates illumination light from the lighting unit 40 to a forward side of the insertion portion 10. The projection window 13 radiates a stripe pattern from the pattern projector 50 to the forward side of the insertion portion 10.

The imaging unit 30 includes an imager 31, the objective optical system 32 and an imager controller (a controller) 33. The imager 31 is disposed in the vicinity of a distal end of the insertion portion 10. The objective optical system 32 is disposed in front of the imager 31. The imager controller 33 is connected to the imager 31.

An area image sensor having, for example, a rectangular sensor region in which square-shaped pixels are arranged in a lattice shape and configured to image an image by detecting a light quantity that enters the sensor region at every pixel can be employed as the imager 31. In the embodiment, in the image imaged by the imager 31, a short side of the sensor region of the imager 31 is represented as a vertical side. In addition, a long side of the sensor region of the imager 31 is represented as a horizontal side. As a specific example of the imager 31, various known constitutions including various kinds of image sensors such as CCD, CMOS, and so on, may be appropriately selected and used.

The objective optical system 32 is disposed in the opening 11 of the insertion portion 10. The objective optical system 32 has a predetermined angle of view (view angle). The objective optical system 32 allows the reflected light in the observation field of view defined by the angle of view to enter the imager 31, and forms the image of the specimen. In addition, the objective optical system 32 has a cover member 32a having optical transparency. The cover member 32a seals the opening 11.

The imager controller 33 is provided in the main body portion 20. In addition, the imager controller 33 is connected to the imager 31 by a wiring 34 extending in the insertion portion 10. The imager controller 33 performs various kinds of controls such as driving of the imager 31, setting of acquiring a video signal, and so on.

The lighting unit 40 includes a first light source 41, a lighting optical system 42, a first fiber bundle 43, and a first incident optical system 44. The first fiber bundle 43 guides light of the first light source 41 to the lighting optical system 42. The first incident optical system 44 is disposed between the first light source 41 and the first fiber bundle 43.

The first light source 41 is a light source configured to emit white light. The first light source 41 is disposed in the main body portion 20. A known light source such as a halogen or mercury lamp, or the like, may be appropriately selected and employed as the first light source 41. In the embodiment, the halogen lamp is employed as the first light source 41. The light emitted from the first light source 41 is illumination light used to illuminate the specimen.

The lighting optical system 42 is attached to the distal end of the insertion portion 10 or the vicinity of the distal end. The lighting optical system 42 has a cover member 42a having optical transparency, and a group of lenses (not shown). The cover member 42a is provided in the lighting window 12 of the insertion portion 10. The lighting optical system 42 spreads the light radiated from the first light source 41 to a range of a field of view appropriate for an angle of view of the objective optical system 32 and emits the light from the lighting window 12, illuminating all of the observation field of view.

The first fiber bundle 43 extends from the vicinity of the lighting optical system 42 to the vicinity of the first light source 41 in the main body portion 20 through the insertion portion 10. The kind of the first fiber bundle 43 is not particularly limited, and a conventional light guide may be used.

The first incident optical system 44 collects the light emitted from the first light source 41 to substantially the same diameter as that of the first fiber bundle 43 and efficiently guides the light into the first fiber bundle 43.

The pattern projector 50 includes a second light source 51, a projection optical system 52, a second fiber bundle 53, a second incident optical system 54, and a pattern generator 55. The second fiber bundle 53 guides the light of the second light source 51 to the projection optical system 52. The second incident optical system 54 is disposed between the second light source 51 and the second fiber bundle 53. The pattern generator 55 is disposed on an optical path of the light emitted from the second light source 51.

The second light source 51 is a light source configured to emit different light from the first light source 41. The second light source 51 is disposed in the main body portion 20. An LED light source, a laser light source, or the like, may be employed as the second light source 51. In the embodiment, the LED light source is employed as the second light source 51. The light emitted from the second light source 51 is projection light used to project a stripe pattern.

The projection optical system 52 is attached to the distal end of the insertion portion 10 or the vicinity of the distal end. The projection optical system 52 has a cover member 52a having optical transparency. The cover member 52a is provided in the projection window 13 of the insertion portion 10. As shown in FIG. 2, the projection window 13 is disposed at a position adjacent to a short side of the imager 31 when seen from a side of the distal surface 10a of the insertion portion 10.

In addition, the cover member 52a provided at the projection window 13 may have a lens shape. The projection optical system 52 projects the light radiated from the second light source 51 into the observation field of view from the one projection window 13 at a predetermined radiation angle corresponding to the angle of view of the objective optical system 32.

Here, a relation between the angle of view of the objective optical system 32 and the radiation angle of the projection light by the projection optical system 52 in the embodiment is described.

Figure 3:
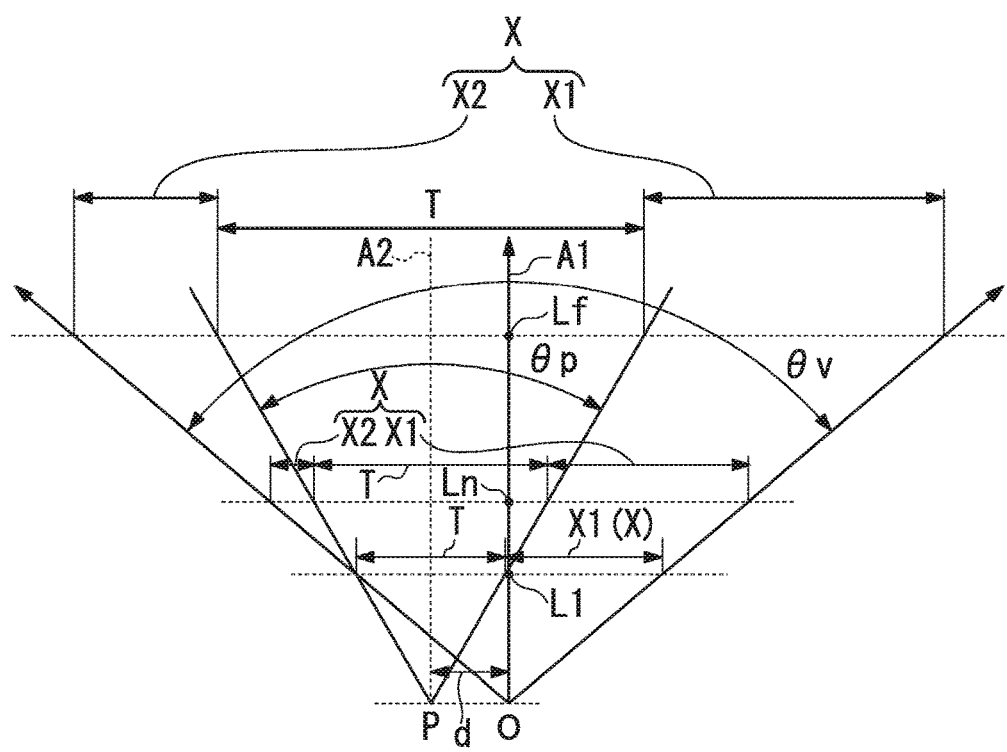
FIG. 3 is a schematic view showing a relation between an angle of view of an objective optical system and a radiation angle by a projection optical system in the endoscope according to the embodiment of the present invention.

FIG. 3 is a schematic view showing the relation between the angle of view of the objective optical system 32 and the radiation angle of the projection optical system 52. In FIG. 3, reference character O represents a position of the objective optical system 32. Further, reference character P represents a position of the projection optical system 52.

As shown in FIG. 3, in the embodiment, an angle of view $\theta v$ of the objective optical system 32 is spread to equal angles using a depth direction of the objective optical system 32 (a direction of an object distance) as a centerline (shown by reference character A1 in FIG. 3). In addition, a radiation angle $\theta p$ of the projection optical system 52 is spread to equal angles about a centerline A2 parallel to a centerline A1. Further, the angle of view $\theta v$ of the objective optical system 32 and the radiation angle $\theta p$ of the projection optical system 52 satisfy $\theta v > \theta p$.

In addition, provided that a depth of a near point side of the objective optical system 32 is represented by Ln and a depth of a far point side thereof is represented by Lf, the shortest object distance L1 at which the entire projected stripe enters the field of view satisfies $Ln \geq L1$.

According to the above-mentioned relation, when the object distance is in focus (within a depth from Ln to Lf), the entire stripe pattern is disposed in the angle of view of the objective optical system 32.

In addition, in the embodiment, a distance d between a center of the objective optical system 32 and a center of the projection optical system 52 is set to be smaller than a depth L1, which is a minimum value of the measurable object distance. For this reason, the distance d is sufficiently smaller than the object distance Ln. For this reason, within a range in which the imaging unit 30 is in focus, a position of the stripe taken in the image is not largely varied.

As shown in FIG. 1, the second fiber bundle 53 extends from the vicinity of the projection optical system 52 to the vicinity of the second light source 51 in the main body portion 20 through the insertion portion 10. Like the first fiber bundle 43, a general light guide may be used as the second fiber bundle 53.

The second incident optical system 54 collects the light emitted from the second light source 51 to substantially the same diameter as that of the second fiber bundle 53 and efficiently guides the light into the second fiber bundle 53.

The pattern generator 55 is configured to be capable of forming the stripe pattern. For example, a slit plate having a plurality of slits, or a transparent plate, on which a stripe pattern is drawn, formed of glass, resin, or the like, may be used as the pattern generator 55. The stripe pattern is preferably a strip-shaped stripe pattern in which brightness of the stripes is smoothly and periodically varied. In addition, the stripe pattern may be a stripe pattern in which a white or black color has a rectangular shape and brightness thereof is varied.

The stripe pattern in the embodiment is a pattern extending in a short-side direction of the sensor region of the imager 31 and disposed in parallel in a long-side direction of the sensor region of the imager 31 at a predetermined interval (see FIG. 2). That is, in the embodiment, the stripe pattern extends in a vertical direction of the image acquired by the imaging unit 30 when the stripe pattern is projected on a plane facing the distal end of the insertion portion. In addition, here, the stripe pattern is taken as lines disposed in parallel in a horizontal direction (see FIG. 4).

Moreover, a liquid crystal shutter module configured to be capable of switching transmission and non-transmission of the light at every device, a microelectromechanical system (MEMS) mirror module including a fine reflective mirror at every device, or the like may be used as the pattern generator 55. In this case, since each device is individually controlled and the stripe pattern having an appropriate phase can be formed without moving the entire pattern generator 55, the constitution of the pattern projector 50 can be simplified. Switching of the stripe pattern is performed by a pattern controller (a controller) 56 connected to the pattern generator 55.

Figure 4:
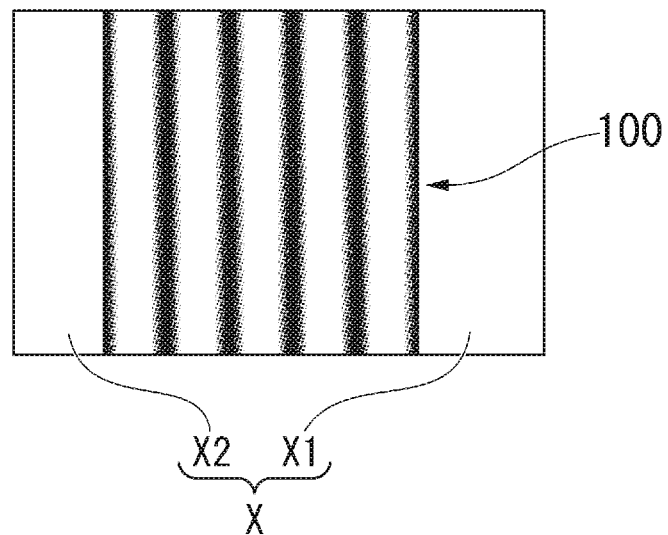
FIG. 4 is a schematic view showing an example of a pattern projection image displayed on a monitor of the endoscope according to the embodiment of the present invention.

FIG. 4 is a schematic view showing an example of a stripe pattern projected on the specimen.

As shown in FIG. 3, as the angle of view $\theta v$ of the objective optical system 32 and the radiation angle $\theta p$ of the projection optical system 52 have the above-mentioned relation, as shown in FIG. 4, the pattern projector 50 projects a stripe pattern 100 on the specimen. In this state, non-projection regions X in which the stripe pattern is not projected (a right non-projection region X1 and a left non-projection region X2) are formed at both ends in a direction in which the stripes of the stripe pattern are arranged in the imaging field of view of the imaging unit 30.

In addition, the relation between the angle of view of the objective optical system 32 and the radiation angle of the projection light in the projection optical system 52 may satisfy $\theta p \geq \theta v$. In this case, while the stripe pattern is not entirely disposed in the angle of view of the objective optical system 32, the non-projection region X (the right non-projection region X1 or the left non-projection region X2) in which the stripe pattern is not projected is formed at one of both directions in which the stripes of the stripe pattern are arranged in the imaging field of view.

The above-mentioned imager controller 33, a light source controller (a controller) 21, and a main controller (a controller) 22 are provided in the main body portion 20. The light source controller 21 controls an operation of emitting the illumination light from the lighting unit 40 and an operation of emitting the projection light from the pattern projector 50.

A video processor 27 and the main controller 22 are connected to the imager controller 33. The video processor 27 processes a video signal acquired by the imager 31. The main controller 22 controls an operation of the imager controller 33. The video processor 27 and the main controller 22 are provided in the main body portion 20.

A monitor (a display) 28 is connected to the video processor 27. The monitor 28 displays the video signal processed by the video processor 27 as the image. The video processor 27 generates an image, which is a frame F showing a predicted projection position on the display screen of the stripe pattern projected on the specimen, and outputs the image to the monitor 28 to overlap the image acquired by the imaging unit 30.

Since the distance d shown in FIG. 3 is substantially smaller than the object distance Ln or the object distance Lf, the position of the stripe pattern displayed on the monitor 28 is moved leftward and rightward within a certain level of range without a large variation. That is, the position of the stripe pattern slightly moves on the image displayed on the monitor 28 in the horizontal direction according to the object distance with respect to the specimen.

Figure 5A:
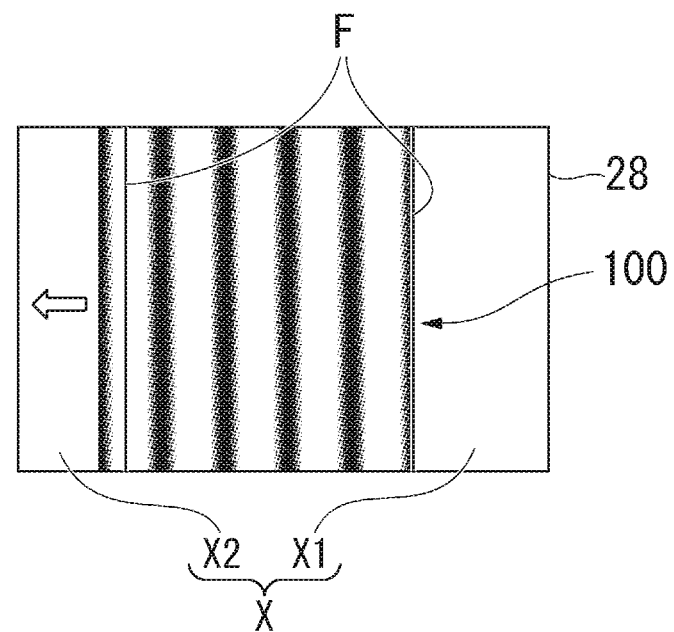
FIG. 5A is a schematic view showing a frame displayed on the monitor of the endoscope according to the embodiment of the present invention.
Figure 5B:
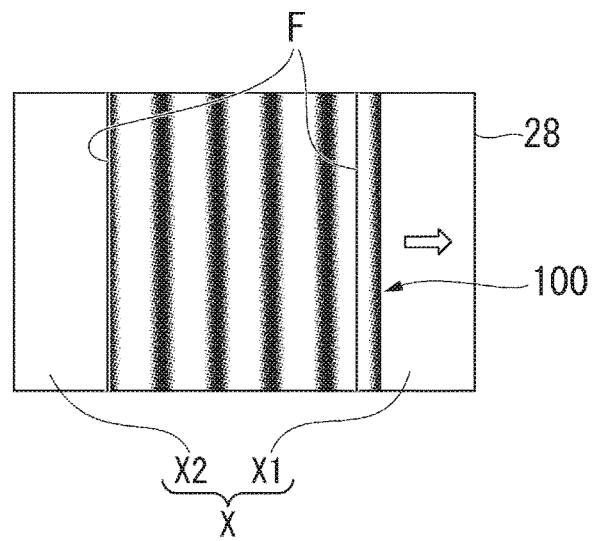
FIG. 5B is a schematic view showing the frame displayed on the monitor of the endoscope according to the embodiment of the present invention.

FIGS. 5A and 5B are schematic views showing the frame F displayed on the monitor of the endoscope 1. As shown in FIGS. 5A and 5B, in the embodiment, even when the stripe pattern 100 is maximally moved in the horizontal direction, the position of the frame F is set to surround a region on which the stripe pattern 100 is displayed. Accordingly, the stripe pattern 100 is disposed in the frame F regardless of an actual position of the stripe pattern 100 in the image displayed on the monitor 28. When the position of the frame F is set as described above, there is no need to adjust the position of the frame F in accordance with the position of the stripe pattern 100. For this reason, processing of displaying the frame F is simplified.

The monitor 28 displays the image of the specimen and the frame F showing the predicted projection position of the stripe pattern on the display screen. In addition, the measurement result of the three-dimensional shape or various kinds of information detected in use of the endoscope 1 are displayed on the monitor 28.

As shown in FIG. 1, the light source controller 21 is connected to the first light source 41, the second light source 51, and the main controller 22. The light source controller 21 controls ON/OFF of the first light source 41 and the second light source 51 based on the control by the main controller 22.

The main controller 22 is further connected to an operating unit 23, a RAM 24, a ROM 26, an auxiliary storage device 25, and the pattern controller 56.

The operating unit 23 has switches configured to allow a user to perform various kinds of inputs to the endoscope 1, and so on.

In addition, a touch panel provided to overlap the display screen of the monitor 28 may be employed as the operating unit 23.

The RAM 24 functions as a work area used upon imaging of the specimen using the endoscope 1, measurement of the three-dimensional shape of the specimen using the endoscope 1, or the like.

For example, firmware or the like is recorded on the ROM 26. The ROM 26 is configured such that the firmware or the like is read upon starting of the endoscope 1.

The auxiliary storage device 25 may employ, for example, a storage device or a magnetic storage device having a non-volatile memory which is rewritable.

The main controller 22 sets the region on the image surrounded by the frame F generated by the video processor 27 to a target region T (see FIG. 3) used for measuring the three-dimensional shape, and obtains the three-dimensional shape of the specimen with respect to the inside of the target region T only.

As a measurement method for measuring the three-dimensional shape of the specimen by the main controller 22, a method of obtaining a phase of the stripe pattern by a phase shift method, a Fourier transform method, or the like, and calculating the three-dimensional shape of the specimen based on the phase of the stripe pattern may be used.

An operation of the endoscope having the above-mentioned constitution is described.

In use of the endoscope 1, first, a user inserts the insertion portion 10 shown in FIG. 1 into the inside of the specimen, the access path to the specimen such as the conduit line or the like, or the like, and moves the distal end of the insertion portion 10 forward to a predetermined observation area. The user performs inspection or the like of the specimen by switching an observation mode for observing a predetermined area of the specimen and a measurement mode for measuring a three-dimensional shape of the observation area as needed.

In the observation mode, the light source controller 21 that receives an order of the main controller 22 shown in FIG. 1 turns the first light source 41 on and turns the second light source 51 off. As a result, the white light is radiated from the lighting unit 40 to the observation field of view while the stripe pattern is not projected from the pattern projector 50, and the observation field of view is illuminated (hereinafter, this illumination state is referred to as an "observation state"). The image of the illuminated specimen is imaged by the imager 31 through the objective optical system 32. The video signal transmitted from the imager 31 is processed by the video processor 27 and displayed on the monitor 28. The user can observe the specimen by the image of the specimen displayed on the monitor 28 and save the image as needed.

When the observation mode is switched to the measurement mode, the user inputs an order of switching the mode. When the user performs the input of switching from the observation mode to the measurement mode, a control signal for displaying the image of the frame F on the monitor 28 is output from the main controller 22 to the video processor 27. Accordingly, the image of the frame F corresponding to the predicted projection position of the stripe pattern is displayed on the monitor 28 (see FIGS. 5A and 5B).

In addition, in this state, the stripe pattern 100 is still not projected, and the user can observe the image of the specimen illuminated by the illumination light.

The user adjusts the position of the insertion portion 10 or the like such that an area of the specimen that requires measurement of the three-dimensional shape enters the frame F on the monitor 28. In a state in which the required area is disposed in the frame F displayed on the monitor 28, the user starts the measurement of the three-dimensional shape using the switch or the like (not shown) of the operating unit 23.

When the measurement of the three-dimensional shape is started, first, at least one image is acquired by the imaging unit 30 in a state in which the illumination light from the lighting unit 40 shown in FIG. 1 is radiated. Next, radiation of the illumination light from the first light source 41 of the lighting unit 40 is stopped by the light source controller 21, and radiation of the projection light from the second light source 51 of the pattern projector 50 is started by the light source controller 21.

When the projection light is radiated, the projection light passes through the pattern generator 55 and the projection optical system 52, and the stripe pattern is projected on the specimen.

As shown in FIG. 3, when the stripe pattern is projected on an object, the stripe pattern is projected on a portion in the angle of view of the objective optical system 32, and the non-projection regions X in which the stripe pattern is not projected are generated at both ends in a direction in which the stripes of the stripe pattern are arranged in parallel in the imaging field of view of the imaging unit 30.

In addition, the positions of the stripe patterns in the angle of view of the objective optical system 32 are different in accordance with the object distance. However, in the embodiment, since the distance d between the center of the objective optical system 32 and the center of the projection optical system 52 is set to be sufficiently smaller than a measurable object distance, the position at which the stripe is displayed on the screen is not varied largely. For this reason, even when the position of the stripe pattern is moved, the position of the stripe pattern is configured to be kept within substantially the frame F, which is previously set (see FIGS. 5A and 5B).

In a state in which the stripe pattern is projected on the specimen, the imaging unit 30 acquires the image of the specimen.

The image of the specimen on which the stripe pattern is projected is output to the main controller 22 via the video processor 27 shown in FIG. 1 as the stripe image. In addition, the image of the specimen is temporarily stored in the RAM 24 or the like.

Next, the phase of the stripe pattern is obtained from one pattern projection image acquired by the imaging unit 30 through the above-mentioned phase shift method, the Fourier transform method, or the like, by the main controller 22.

In addition, when the measurement of the three-dimensional shape is performed using a temporal phase shift method, a plurality of pattern projection images having different phases are imaged by the imaging unit 30, and the phase of the stripe pattern photographed in the plurality of pattern projection images is obtained by the main controller 22. In the endoscope 1 according to the embodiment, the non-projection region X in which the stripe pattern is not projected is generated in at least a portion of each of the plurality of imaged pattern projection images. For this reason, correspondence between the stripe photographed on the pattern projection image and the stripe of the projected stripe pattern is relatively easily performed using a boundary between the region on which the stripe pattern is projected and the non-projection region X as a starting point. Accordingly, three-dimensional coordinates in a real space can be calculated from the obtained phase. Next, when the target region T which becomes a target in which the three-dimensional shape of the specimen is measured (i.e., a measurable range of the field of view) is set to a region inside the frame F, as distribution of the three-dimensional coordinates in the target region T is obtained, the three-dimensional shape of the specimen can be obtained. In addition, calculation of measuring the three-dimensional shape of the specimen is not limited in the target region T but may be performed within a range in which the light and dark pattern is photographed.

The result calculated by the main controller 22 is output to the video processor 27 to be displayed on the monitor 28 as a numerical value or an image. In addition, the calculated result is received into the auxiliary storage device 25 as a file.

As the calculated result is displayed on the monitor 28, the user can recognize the three-dimensional shape of the specimen in the frame F.

As described above, according to the endoscope 1 according to the embodiment, as the non-projection regions X in which the stripe pattern is not projected are generated in both ends or one ends in a direction in which the stripes of the stripe pattern are arranged in the imaging field of view of the imaging unit 30, it is possible to easily match the stripes photographed in the pattern projection image to the stripes projected on the specimen. Accordingly, the object distance of the specimen can be obtained by measurement of the pattern projection image.

While a method of forming two openings in which the projection optical system 52 is disposed and projecting the stripe patterns from two directions is known as another method of easily matching the stripe pattern photographed on the pattern projection image to the stripe pattern projected on the specimen, in the embodiment, since it is only necessary to form only one opening in which the projection optical system 52 is disposed in the distal portion of the insertion portion 10, the insertion portion 10 can be further reduced in diameter. Alternatively, while a method of measuring the three-dimensional shape of the specimen simultaneously using sensors configured to separately measure the stripe pattern projected on the specimen and the object distance of the specimen is known, in the embodiment, since there is no need to mount the sensor configured to separately measure the object distance of the specimen, the insertion portion 10 can be further reduced in diameter.

In addition, when the specimen is in focus, since the non-projection region X should be generated on the pattern projection image, the user only focuses the specimen and starts the measurement of the three-dimensional shape, and the operation of the endoscope 1 becomes convenient.

Further, since the non-projection region is generated in both ends or one end in the direction in which the stripes of the stripe pattern are arranged in the imaging field of view of the imaging unit, it is relatively easy to match the stripe pattern photographed on the pattern projection image to the projected stripe pattern. For this reason, misrecognition upon analysis of the stripe pattern can be reduced. In addition, deterioration of reliability of the measurement value or measurement performance can be prevented.

Further, since the frame F showing the predicted projection position of the stripe pattern projected on the specimen is displayed on the display screen of the monitor 28 by the main controller 22 and the video processor 27, in use of the endoscope 1, the region in which the three-dimensional shape can be measured can be recognized by the user.

In addition, since the stripe pattern is projected into substantially the frame F even when the position of the stripe pattern is varied in accordance with the object distance, there is no need to actually project the stripe pattern to recognize the region in which the three-dimensional shape can be measured, and the measurement operation by the endoscope can be simplified.

Further, when the main controller 22 measures the three-dimensional shape with respect to only the target region T using the inside of the frame F as the target region T, a calculation amount can be reduced more than when the stripe pattern is photographed on the entire image and the three-dimensional shape is calculated at the entire region of the image. In addition, in this case, the calculation result of the three-dimensional shape can be rapidly obtained.

Further, since the radiation angle of the projection light is smaller than the angle of view of the objective optical system 32, the projection window 13 can be reduced in size in comparison with the case in which the radiation angle of the projection light is larger than the angle of view of the objective optical system 32. For this reason, the insertion portion 10 can be further reduced in diameter.

(Modified Example 1)

Next, a modified example of the endoscope 1 described in the above-mentioned embodiment is described.

Figure 6:
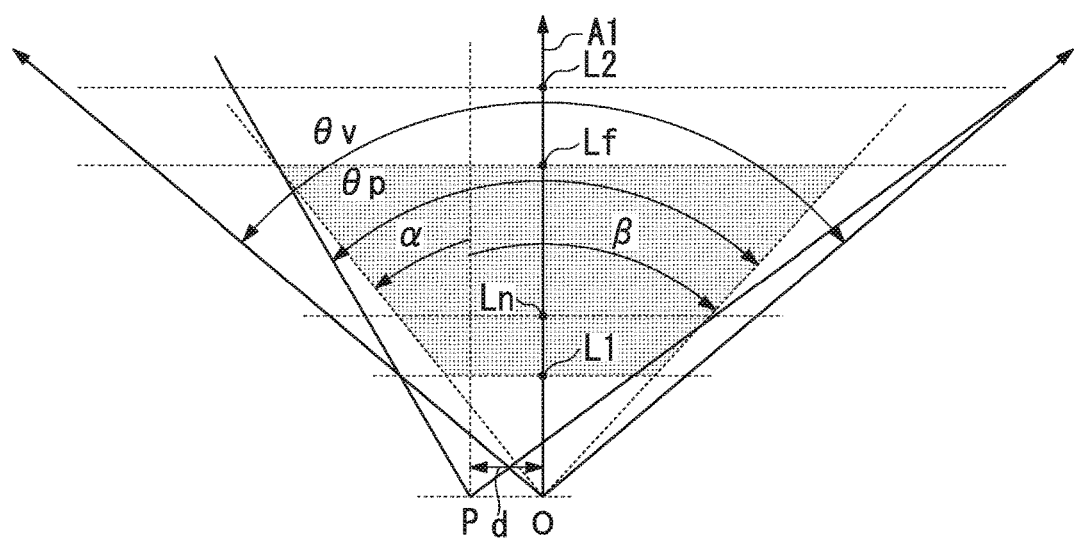
FIG. 6 is a schematic view showing a relation between an angle of view of an objective optical system and a radiation angle by a projection optical system in a modified example of the endoscope according to the embodiment of the present invention.

FIG. 6 is a schematic view showing a relation between the angle of view $\theta v$ of the objective optical system 32 and the radiation angle $\theta p$ of the projection optical system 52 in the modified example.

In FIG. 6, reference character $\alpha$ and reference character $\beta$ represent radiation angles of the projection light by the projection optical system 52. Specifically, reference character $\alpha$ represents a left radiation angle with respect to a depth direction of the objective optical system 32. Reference character $\beta$ represents a right radiation angle with respect to the depth direction of the objective optical system 32. The other reference characters shown in FIG. 6 are the same as described in the above-mentioned embodiment.

As shown in FIG. 6, a magnitude of the radiation angle $\theta p$ of the projection light by the projection optical system 52 is a sum of the left radiation angle $\alpha$ and the right radiation angle $\beta$. The modified example has a different constitution from the above-mentioned embodiment in that the radiation angle θp of the projection light does not have equal left and right angles with respect to a centerline in the depth direction.

In the modified example, when the object distance in which all the projected stripes enter the angle of view of the objective optical system 32 is within a range from L1 to L2, Ln≥L1 and Lf≤L2 are satisfied, and further, when the object distance is within the depth (a range from Ln to Lf), all the stripes can be photographed in the field of view.

In addition, here, the angle of view θv of the objective optical system 32 and the radiation angle θp of the stripe projection satisfy a relation of θv>θp.

Even when the angle of view θv of the objective optical system 32 and the radiation angle θp of the projection light have the above-mentioned relation, like the above-mentioned embodiment, the non-projection region X in which the stripe pattern is not projected can be generated at one end in the direction in which the stripes of the stripe pattern are arranged in the imaging field of view of the imaging unit 30.

(Modified Example 2)

Next, another modified example of the endoscope 1 described in the above-mentioned embodiment is described.

In the modified example, the video processor 27 configured to generate the image of the frame F further includes a unit configured to adjust the position of the frame F.

In the method of setting the frame F in the endoscope 1 according to the above-mentioned embodiment, the stripe pattern may be actually displayed even in the region outside the frame F. As a unit configured to vary the position of the frame F in accordance with the projection position of the actual stripe pattern is further provided, the region in which the three-dimensional shape can be measured can be more accurately seen by the user.

Specifically, the unit configured to adjust the shape of the frame F rapidly detects both of left and right ends of the plurality of stripes in the stripe pattern and displays the frame F in accordance with a contour of the stripe pattern. Here, constant projection of the stripe pattern interferes with observation of the specimen. For this reason, for example, the projection of the stripe pattern is performed only for a short time within a range that does not interfere with the observation, for example, projection of the stripe pattern on the specimen only for $\frac{1}{30}$ of a second. As a method of rapidly detecting both of left and right ends of the stripe, the image of the specimen is acquired in a state in which the stripe pattern is projected, and edge detection of the stripe from the acquired image is performed.

The edge detection may be limited to a portion such as only one line of a central portion of the image, or only a predetermined plurality of lines. Accordingly, a calculation amount for the edge detection can be reduced.

In addition, when a calculation speed for the edge detection can be substantially obtained, in order to more accurately display the frame F, the frame F may be displayed from the edge detection result in all the lines on the image.

Further, the display of the frame F is updated at a predetermined interval, for example, every second. Since the projection itself of the stripe pattern is performed for a short time not to interfere with radiation of the illumination light to the specimen and observation of the specimen, the frame F can be displayed on the monitor 28 in substantially real time without interference with observation of the object on the screen.

As described above, in the modified example, the shape of the frame F is set based on the stripe pattern actually projected on the specimen. For this reason, in comparison with the case in which the frame F is set by the method described in the above-mentioned embodiment, the region in which the three-dimensional shape can be measured can be seen by the user exactly.

In addition, since the display of the frame F is updated at a predetermined interval, the region in which the stripe pattern is actually projected can be updated to the latest state at a predetermined interval. For this reason, the probability of not projecting the stripe pattern in the frame F can be reduced.

While the above-mentioned embodiment has been described using the example in which the opening in which the objective optical system is disposed, the opening in which the lighting optical system is disposed, and the opening in which the projection optical system is disposed are formed one by one, each of these openings may be formed by two or more.

In addition, while the above-mentioned embodiment shows the example in which the projector configured to project the stripes extending in the vertical direction of the image imaged by the imaging unit is arranged with respect to the objective optical system in the horizontal direction, the projector configured to project the stripes extending in the horizontal direction of the image imaged by the imaging unit may be arranged with respect to the objective optical system in the vertical direction. Alternatively, a shape of the light and dark pattern may be a lattice-shaped pattern in which pluralities of vertical bands and horizontal bands cross each other, or a plurality of points arranged in vertical and horizontal directions at equal intervals, rather than the band-shaped stripes.

In addition, while the above-mentioned embodiment shows the example in which the first light source configured to radiate the illumination light and the second light source configured to radiate the projection light are disposed in the main body portion, the first light source and the second light source may be provided at the distal end of the insertion portion.

Further, the first light source and the second light source may include a shutter, a mirror module, or the like, configured to switch a radiation state of the light. In this case, a light source in which lighting on/off is time-consuming can also be used as an appropriate light source.

Furthermore, the shape of the frame may be set as an appropriate shape such as a round shape, a rectangular shape, and other polygonal shapes, in addition to the shape shown in the above-mentioned embodiment.

In addition, while the above-mentioned embodiment exemplarily shows the constitution in which the non-projection regions are generated at both ends in the direction in which the stripes of the stripe pattern are arranged in the imaging field of view of the imaging unit, a constitution in which the non-projection region is generated at one end in the direction in which the stripes of the stripe pattern are arranged in the imaging field of view of the imaging unit may be provided. When the non-projection region is generated at the one end in the direction in which the stripes of the stripe pattern are arranged in the imaging field of view of the imaging unit, the boundary between the non-projection region and the stripe pattern can be detected by the edge detection or the like. In addition, in this case, it is possible to match the stripes of the projected stripe pattern to the stripes on the image using the boundary between the non-projection region and the stripe pattern as a starting point.

Further, instead of the stripe pattern generator described in the above-mentioned embodiment, a generator configured to generate a pattern such as a lattice shape, a dotted shape, or the like, may be provided.

Hereinabove, while preferred embodiment of the present invention has been described, the present invention is not limited to the embodiment. Additions, omissions, substitutions, and other modifications can be made to the present invention without departing from the spirit and scope of the present invention. The present invention is not limited to the above-mentioned description, and is only limited by the appended claims.

What is claimed is:

1. An endoscope configured to measure a specimen using a stripe image formed by projecting a light-dark pattern on the specimen, the endoscope comprising:
    an insertion portion having an elongated shape;
    an imaging unit provided at a distal portion of the insertion portion and configured to acquire an image of the specimen;
    a lighting unit configured to illuminate an observation field of view of the imaging unit; and
    a pattern projector which emits projection light configured to project the light-dark pattern to the specimen and project the light-dark pattern on the specimen,
    wherein the imaging unit includes:
        an image sensor configured to image the image of the specimen; and
        an objective optical system configured to form the image of the specimen on the image sensor,
    wherein the pattern projector includes:
        a pattern generator configured to generate the light-dark pattern; and
        a projection optical system provided at the distal portion of the insertion portion and configured to emit the projection light to the specimen via the light-dark pattern,
    wherein a radiation angle of the projection light in the projection optical system is smaller than an angle of view of the objective optical system, and
    wherein the objective optical system is in focus at a farther point side than a minimum object distance which is a minimum value of an object distance at which the entire projected light-dark pattern enters an imaging field of view of the image sensor.

2. The endoscope according to claim 1, wherein a distance between a center of the objective optical system and a center of the projection optical system is smaller than the minimum object distance.

3. The endoscope according to claim 1, wherein the pattern projector produces a region in which the light-dark pattern is not projected and which is on at least one side of the imaging field of view of the imaging unit relative to a direction in which stripes of the light-dark pattern are arranged, in a state in which the light-dark pattern is projected on the specimen.

4. The endoscope according to claim 3, wherein when a magnitude of the radiation angle of the projection light is a sum of a left radiation angle and the left radiation angle, the left radiation angle and the right radiation angle are different, the left radiation angle being a left radiation angle with respect to a centerline in a depth direction of the objective optical system, and the right radiation angle being a right radiation angle with respect to the centerline.

5. The endoscope according to claim 3, further comprising a display which has a display screen configured to display the image of the specimen and displays a frame on the display screen, the frame showing a predicted projection position on the display screen of the stripe pattern projected on the specimen.

6. The endoscope according to claim 5, wherein the display displays the frame on the display screen even when the light-dark pattern is not projected on the specimen.

7. The endoscope according to claim 6, further comprising a controller configured to switch an observation mode for observing the specimen and a measurement mode for measuring the specimen,
    wherein the display configured to display the frame on the display screen when the controller switches to the measurement mode from the observation mode.

8. The endoscope according to claim 5, further comprising a video processor configured to generate an image of the frame, overlap the image of the frame onto the image of the specimen acquired by the imaging unit, and output the overlapped image to the display.

9. The endoscope according to claim 8, wherein the video processor overlaps the image of the frame onto the image of the specimen even when the light-dark pattern is not projected on the specimen.

10. The endoscope according to claim 9, further comprising a controller configured to switch an observation mode for observing the specimen and a measurement mode for measuring the specimen,
    wherein the video processor overlaps the image of the frame onto the image of the specimen when the controller switches to the measurement mode from the observation mode.

11. The endoscope according to claim 5, further comprising a controller configured to measure the specimen using only the image of specimen displayed within the frame.

* * * * *